US00PP07779P

United States Patent [19]

Wilms

[11] Patent Number: Plant 7,779

[45] Date of Patent: Feb. 4, 1992

[54] DAHLIA PLANT NAMED LINDA

[75] Inventor: His J. Wilms, Wognum, Netherlands

[73] Assignee: Royal Sluis, Enkhuizen, Netherlands

[21] Appl. No.: 570,318

[22] Filed: Aug. 21, 1990

[51] Int. Cl.[5] ..... A01H 5/00

[52] U.S. Cl. ..... Plt./68

[58] Field of Search ..... Plt. 68

*Primary Examiner*—James R. Feyrer

*Attorney, Agent, or Firm*—Foley & Lardner

[57] ABSTRACT

A new and distinct dahlia plant named Linda, having pure yellow-orange flower color, double flower form, dense foliage, continuous flowering, compact flower bouquet carried above the foliage, compact growth habit, and an adaptability to pot plant or natural outdoor cultures.

1 Drawing Sheet

The present invention relates to a new and distinct cultivar of dahlia plant known by the cultivar name Linda, and botanically known as Dahlia Cav.

Linda is a product of breeding and mutation induction programs. The parents were selected plants used in the 1984 breeding program, and are not presently identifiable. The cross was made by the inventor in Enkhuizen, the Netherlands, in 1984. The parents were descendants from the variety Figaro, a well known seed dahlia, which has created a standard for flower form, habit and leaf size. The breeding line selected out of the progeny of the stated cross was designated breeding line number 85212 (light orange).

Plants from this selected breeding line were subjected to 2,500 rads of gamma radiation, after which cuttings of the irradiated plants were taken. The cuttings were stuck, grown and allowed to flower, and selections made. Selections were based primarily on intensive and unique flower color, early flowering, and large flower diameter, with all of these traits being very significant commercially. Linda was selected and identified by selection No. 86227, and possesses all of these characteristics, especially its beautiful, intense yellow-orange flower color.

The first act of asexual reproduction of Linda was accomplished when tuberous divisions were taken by the inventor from the new cultivar after discovery in a controlled environment in Enkhuizen, The Netherlands. Subsequent horticultural examination of selected units has demonstrated that the combination of characteristics as herein disclosed for Linda are firmly fixed and are retained through successive generations of asexual reproduction. The new cultivar cannot be propagated true to type by seed.

Linda has not been observed under all possible environmental conditions. The phenotype may vary significantly with variations in environment such as temperature, light intensity, and day length. The following observations, measurements and comparisons describe plants grown in Enkhuizen, The Netherlands under greenhouse and outdoor conditions which approximate those generally used in commercial practice.

The following traits have been repeatedly observed and are determined to be basic characteristics of Linda, which in combination distinguish this dahlia as a new and distinct cultivar:

1. Intense and pure yellow-orange ray floret color.
2. Double flower form, and large flower diameter.
3. Dense foliage.

4. Early flowering.
5. Continuous flowering, with the flowers being carried above the foliage.
6. Compact growth habit.
7. Adaptable to pot plant culture as well as natural outdoor growth.
8. Flowers carried on relatively short pedicels.

Relevant cultivars for comparison purposes are the seed varieties Rigoletto and Figaro. In comparison to Rigoletto, Linda is more compact, has a double flower form, and a more pure yellow-orange ray floret color. Linda is distinguished from Figaro by its more compact habit, earlier flowering, and the purity of its yellow-orange ray floret color. Purity refers to a highly uniform color that is not tinged or overlaid. Linda can also be compared to the turberous propagated cultivar Margaret, disclosed in U.S. Plant Pat. No. 6,769. Both cultivars have double flower form, compact growth habit, and continuous flowering. Linda is distinguished from Margaret by Linda's deep orange-yellow color (Margaret is bright yellow), smaller leaves and more compact habit.

The accmpanying color photographic drawing is a perspective view showing typical inflorescence and foliage characteristics of Linda, with colors being as nearly true as possible with illustrations of this type.

In the following description color references are made to The Royal Horticultural Society Colour Chart. The color values were determined at Enkhuizen, The Netherlands, and the characteristics noted below are based on plants grown at the same location.

Classification:

*Botanical.*—*Dahlia cav.* cv Linda (Group IV, peony flowered, classification of International Dahlia Register, 1969).

*Commercial.*—Dahlia.

Parentage:

A selection from an induced irradiation program involving gamma irradiation of plants of the selected breeding line 85212 (light orange), which resulted from a cross of unknown parents.

Plant:

*Form.*—Generally round.

*Size.*—Approximately 21 cm in height (from top of pot) at time of flowering.

*Growth habit.*—Compact.

*Foliage.*—Size: Small, length approximately 6 cm; width approximately 3 cm. Quantity: Abundant, dense. Color: Medium green, approximately 136A. Shape: Generally ovate, edges serrated, tip blunt to slightly pointed. Texture: Relatively dull.

Flowers:

*Form.*—Double.

*Shape.*—Overall inflorescence is generally flat, with petals being generally blunt or slightly rounded tips; firm.

*Size.*—Individual ray florets approximately 3.0 cm long and 2.0 cm wide; overall inflorescence approximately 7 cm in diameter.

*Borne.*—On pedicels which are approximately 4 cm in length (from flower to top part of leaves); top of the pedicel oriented at approximately 100° to the vertical axis of the plant; flowers carried compactly above the foliage; very floriferous.

*Continuity.*—Continuously flowers outdoors after first flower opens.

*Stems.*—Color of new stem is light green, with flowering stem being green.

*Color.*—Fully open: Upper surface 21C. Under surface 11B. Half open: Upper surface 21B. Under surface 16B.

Reproductive organs: Normal.

I claim:

1. A new and distinct cultivar of dahlia plant named Linda, as illustrated and described.

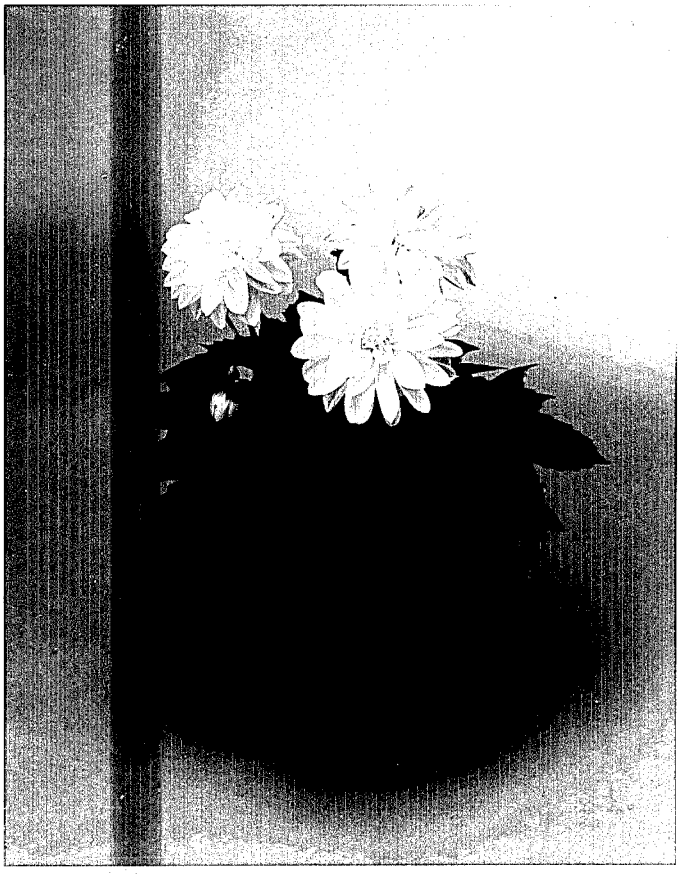

* * * * *